US012624014B2

(12) United States Patent
Huang et al.

(10) Patent No.: US 12,624,014 B2
(45) Date of Patent: May 12, 2026

(54) FLUORESCENT MATERIAL CONTAINING THIOPHENE SULFONE-OLEFIN STRUCTURAL UNIT AND PREPARATION METHOD THEREOF

(71) Applicant: Zhejiang Normal University, Jinhua (CN)

(72) Inventors: Xiaolei Huang, Jinhua (CN); Bingbin Yang, Jinhua (CN); Yaoyao Lu, Jinhua (CN); Yaolin Xia, Jinhua (CN); Xiaoyu Ma, Jinhua (CN)

(73) Assignee: ;Zhejiang Normal University, Jinhua (CN)

( * ) Notice: Subject to any disclaimer, the term of this patent is extended or adjusted under 35 U.S.C. 154(b) by 411 days.

(21) Appl. No.: 18/368,576

(22) Filed: Sep. 15, 2023

(65) Prior Publication Data

US 2024/0166620 A1 May 23, 2024

(30) Foreign Application Priority Data

Nov. 7, 2022 (CN) ......................... 202211386879.9

(51) Int. Cl.
*C07D 333/54* (2006.01)
*C07D 333/56* (2006.01)
*C09K 11/06* (2006.01)

(52) U.S. Cl.
CPC ......... *C07D 333/54* (2013.01); *C07D 333/56* (2013.01); *C09K 11/06* (2013.01); *C09K 2211/1011* (2013.01)

(58) Field of Classification Search
CPC ..... C07D 333/54; C07D 333/56; C09K 11/06
See application file for complete search history.

(56) References Cited

PUBLICATIONS

Ted M. Pappenfus, et al., Synthesis and Electronic Properties of Oxidized Benzo[1,2 b:4,5 b']dithiophenes, The Journal of Organic Chemistry, 2014, pp. 9408-9412, vol. 79.
Peng Ji, et al., Synthesis of Enantioenriched a Deuterated a Amino Acids Enabled by an Organophotocatalytic Radical Approach, Organic Letters, 2020, pp. 1557-1562, vol. 22.

*Primary Examiner* — Brenda L Coleman
(74) *Attorney, Agent, or Firm* — Addison D. Ault; IPGentleman Intellectual Property Services, LLC

(57) ABSTRACT

A fluorescent material containing a thiophene sulfone-olefin structural unit and a preparation method thereof are provided. In the preparation method, the thiophene sulfone compounds, olefins, oxidants and additives are dissolved in the tetrahydrofuran solvent, and are subjected to a reaction under the catalytic action of the palladium catalyst, and the alkenylated thiophene sulfone products with obvious fluorescence emission characteristics of liquid and solid can be obtained. The preparation method expands the range of substrates well, featuring good regional selectivity, high yield, mild reaction conditions and simple operation.

9 Claims, 9 Drawing Sheets

FLUORESCENT MATERIAL CONTAINING THIOPHENE SULFONE-OLEFIN STRUCTURAL UNIT AND PREPARATION METHOD THEREOF

CROSS REFERENCE TO THE RELATED APPLICATIONS

This application is based upon and claims priority to Chinese Patent Application No. 202211386879.9, filed on Nov. 7, 2022, the entire contents of which are incorporated herein by reference.

TECHNICAL FIELD

The present invention belongs to the technical field of organic synthesis, and particularly relates to a fluorescent material containing a thiophene sulfone-olefin structural unit and a preparation method thereof.

BACKGROUND

In recent years; broad application prospects of the thiophene sulfone (S,S-dioxide) skeletons in the field of organic optoelectronic materials have aroused great interest of chemists in synthesis and modification of organic n-conjugated molecules containing thiophene sulfone structural units. For example, Navarrete conducted a Raman spectroscopic analysis of the thiophene sulfone S, S-dioxide-1 in 2005. Compared with a linear and uniform conjugated tertiary thiophene, the introduction of the thiophene sulfone structure led to the division of electronic structure, and the change of this electronic effect makes the design and synthesis of relevant organic material molecules with photoelectric properties feasible; Fattori reported a bithiophene oligomer S, S-dioxide-2 containing a thiophene sulfone structure; which exhibits high photoluminescence quantum efficiency (about 11%) and high oxidation potential (−3.41 eV) in the aggregate state; Leclerc reported a copolymer of fluorene and thiophene Poly-S,S-Dioxide-1, where the introduction of a thiophene oxide led to the formation of an energy gap (2.0 eV), and its luminescence peak wavelength can reach 708 nm, and it is located in the red light region; Yang Wei et al. synthesized blue polymer materials Poly-S, S-Dioxide-2 by using fluorene to copolymerize with sulfur oxyfluorene unit with strong electron affinity, thereby avoiding the problem that classical polyfluorene blue polymer is prone to suffer green light emission under heating conditions.

Some examples of organic photoelectric materials containing thiophene sulfone structural units are as follows:

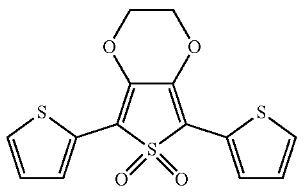

S,S-Dioxide-1

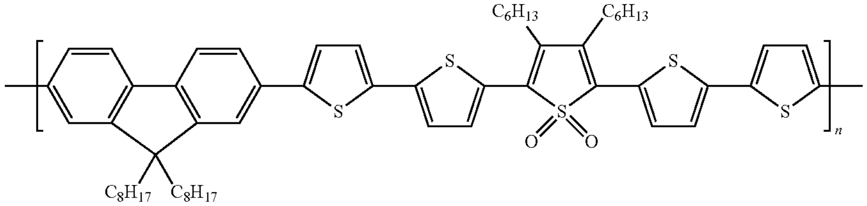

Poly-S,S-Dioxide-1

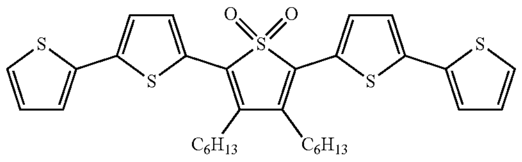

S,S-Dioxide-2

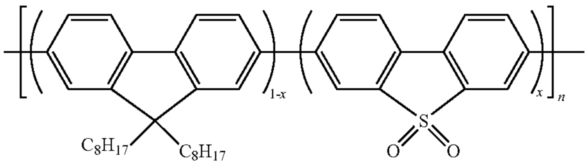

Poly-S,S-Dioxide-2

Traditional synthesis methods of thiophene sulfone fluorescent molecules mainly include oxidation, Diels-Alder reaction, C—X/C—M (M=Sn, B), and the like. These methods have some problems to varying degrees, such as poor functional group tolerance, limited substrate range, and poor environmental friendliness. Therefore, it is of great significance to design a more general and efficient method to synthesize the thiophene sulfone fluorescent molecules.

SUMMARY

In order to solve the problems in the prior art, the present invention provides a novel fluorescent material containing a thiophene sulfone-olefin structural unit with obvious fluorescence emission characteristics. The present invention further provides a preparation method of a fluorescent material containing a thiophene sulfone-olefin structural unit. The reaction process of the preparation method is realized by an oxidized Heck reaction based on C—H bond activation, featuring simple operation, mild reaction conditions, high selectivity of target products and high yield.

In the past decade, the C—H bond activation functionalizati on method has been widely, used in the synthesis of drugs, natural products and organic functional material molecules thanks to its good atom and economic steps and environmental friendliness. Based on the oxidized Heck reaction strategy activated by the C—H bond, the present invention designs the following reaction: thiophene sulfone compounds, olefins, oxidants and additives are dissolved in an organic phase (solvent), and $Pd(OAc)_2$ is used as a catalyst to obtain a new class of a fluorescent material containing a thiophene sulfone-olefin structural unit. Photophysical properties of the material are initially characterized. The results show that the material prepared by the above preparation method has obvious fluorescence emission characteristics. Compared with the traditional transition metal-catalyzed (hetero) arene C—X/C—Sn coupling reaction, the method has the advantages of simple operation, environment protection, high selectivity and good yield.

A fluorescent material containing a thiophene sulfone-olefin structural unit, the structural formula of the fluorescent material containing the thiophene sulfone-olefin structural unit is as follows:

(III)

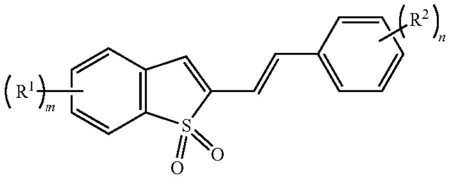

In Formula (III), $R^1$ is one of H, alkyl, halogen, ester group, alkoxy group or trifluoromethyl group; m=1-4; when m≠1, a plurality of $R^1$s are separately selected as one of H, alkyl, halogen, ester group, alkoxy group and trifluoromethyl group. In Formula (III), $R^1$ is one of H, alkyl, halogen, ester group, alkoxy group or trifluoromethyl group; m=1-4; when m≠1, a plurality of $R^1$s are separately selected as one of H, alkyl, halogen, ester group, alkoxy group and trifluoromethyl group.

$R^2$ is one of H, alkyl group, alkoxy group or aryl group; n=1-5; when, a plurality of $R^2$s are separately selected as one of H, alkyl group, alkoxy group or aryl group.

$(R^1)_m$ and $(R_2)_n$ represent one or more substituents in their respective enzene rings. A preparation method of the fluorescent material containing the thiophene sulfone-olefin structural unit, including:

In the presence of a palladium catalyst, thiophene sulfone compounds (substrates), olefins, oxidants and additives are subjected to an oxyalkylene reaction in a solvent, and after the reaction is completed, the fluorescent material containing the thiophene sulfone-olefin structural unit is obtained after post-treatment.

The structural formula of the thiophene sulfone compounds is shown in Formula a):

(I)

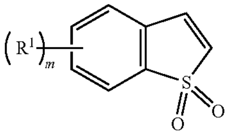

The structural formula of the olefins is shown in Formula (11):

(II)

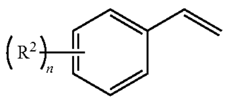

In Formulas (I)-(II), $R^1$ is one of H, alkyl, halogen, ester group, alkoxy group or trifluoromethyl group; m=1-4; when m≠1, a plurality of $R^1$s are separately selected as one of H, alkyl, halogen, ester group, alkoxy group and trifluoromethyl group. In Formula (III), $R^1$ is one of H, alkyl, halogen, ester group, alkoxy group or trifluoromethyl group; m=1-4, when m≠1, a plurality of $R^1$s are separately selected as one of H, alkyl, halogen, ester group, alkoxy group and trifluoromethyl group.

$R^2$ is one of alkyl group, alkoxy group or aryl group; n=1-5; when n≠1, a plurality of $R^2$s are separately selected as one of H, alkyl group, alkoxy group or aryl group.

$(R^1)_m$ and $(R^2)_n$ represent one or more substituents in their benzene rings.

In the above preparation method, the palladium catalyst is $Pd(OAc)_2$, the oxidant is AgOPiv, the additive is PivOH, and the solvent is tetrahydrofuran (THF). The reaction formula of oxidized Heck reaction activated by CHI is specifically shown as follows:

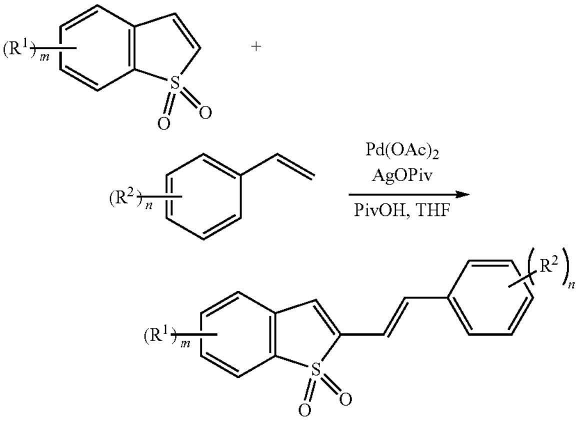

Taking H for both $R^1$ and $R^2$ as an example, a reaction mechanism of the above reaction is as follows:

In the process of reaction, a C—H bond of benzothiophene sulfone is activated to obtain a metal intermediate under the catalysis of a catalytic amount of Pd(II); after then styrene monomer is coordinated, migrated and inserted into Pd to form an intermediate IM3; the IM3 is subjected to a β-H elimination process to obtain a trans-alkenylation product, and HPd(II)OPiv species are released at the same time. Pd(0) species generated by the reduction elimination reaction of HPd(II)OPiv is oxidized by the Ag salt oxidant into an active Pd(II) catalyst, and the reaction cycle is completed.

In the above preparation method, in Formula (II), $R^1$ is an electron-donating group (hydrogen atom, phenyl group, alkyl group, alkoxy group), which enables the reaction to proceed, and the yield thereof falls within the range of good to excellent. The steric hindrance effect has no significant inhibition on activation and cleavage of the C—H bond at a C2 position of the benzothiophene sulfone.

Preferably, in Formula (I), $R^1$ is one of H, alkyl group or alkoxy group. The electron-donating group (H, alkyl group or alkoxy group) enables the reaction to proceed, and the yield thereof falls within the range of good to excellent. When $R^1$ is an electron-withdrawing group (halogen, trifluoromethy, ester group, and the like), the activity of the alkylation reaction is slightly decreased, but the yield falls within the range of medium to good. The steric hindrance effect deliver a great impact on the reactivity of alkenes.

Preferably, a molar ratio of the thiophene sulfone compounds to the olefins is 1:(1-3), further preferably 1:(1.2-1.8), and more preferably 1:1.5.

Preferably, the oxidants can be a monovalent silver salt, such as one or more of silver carbonate, silver acetate, silver oxide, andlorsilver pivalate (AgOPiv), and further preferably the silver pivalate (AgOPiv).

Preferably, a molar ratio of the thiophene sulfone compounds to the oxidants is 1:(1-5), and further preferably 1:(2-4), In order to obtain the best yield, the molar ratio of the thiophene sulfone compounds to the oxidants is more preferably 1:3.

Preferably, the additives can be an acid, such as one or more of pivalic acid (PivOH), acetic acid (AcOH), and trifluoroacetic acid ($CF_3COOH$). The additives are used to activate the catalyst. Further preferably, the additive is PivOH.

Preferably, a molar ratio of the thiophene sulfone compounds to the additives is 1:(3-5), further preferably 1:(3-4). In order to obtain the best yield, the molar ratio of the thiophene sulfone compounds to the additives is more preferably 1:3. Preferably, a molar ratio of the thiophene sulfone compounds, to the olefins, the oxidants and the additives is 1:1.5:3:3.

Preferably, the solvents are at least one of toluene, 1, 2-dichloroethane, 1, 4-dioxane, dimethyl suifoxide, and/or tetrahydrofuran (THE), and further preferably the tetrahydrofuran (THF).

Preferably, the palladium catalyst is $Pd(OAc)_2$ (CAS: 3375-31-3). The catalyst has strong applicability to the substrates in the reaction process of the present invention and can efficiently catalyze the substrates.

Preferably, the amount of the palladium catalyst is 1-5 mol % of the amount of the thiophene sulfone compounds, further preferably 3:5 mol %, further preferably 5 mol %.

Preferably, the reaction temperature of the oxyalkylene reaction is 80-120° C., further preferably 80-100° C., and more preferably 80° C.

Preferably, the oxyalkylene reaction is performed in an air or nitrogen atmosphere, further preferably perform in a nitrogen atmosphere.

Preferably, after the reaction is completed, the following post-treatment is performed:

the reaction mixture is passed through a layer of diatomaceous earth and washed with ethyl acetate, the ethyl acetate/petroleum ether (EtOAc/petroleum ether) is used as eluent, and the washing solution (washing solvent) is purified by silica gel column chromatography to obtain the fluorescent material containing the thiophene sulfone-olefin structural unit.

Preferably, a volume ratio (v/v) of the EtOAc to the petroleum ether in the eluent is 1:(3-6).

The preparation method of the fluorescent material containing the thiophene sulfone-olefin structural unit in the present invention takes the thiophene sulfone compounds and olefins as raw materials, palladium acetate as catalysts, silver pivalate as oxidants, pivalic acid as additives, tetrahydrofuran as solvents, and a compound containing the thiophene sulfone-olefin structural unit as shown in Formula (III) is obtained based on the oxidized Heck reaction strategy activated by the C—H bond. The compound has obvious fluorescence emission characteristics of liquid and solid; and the preparation method expands the range of substrates well, featuring good regional selectivity and high yield.

Compared with the prior art, the present invention has the beneficial effects:

For the preparation method of the fluorescent material containing the thiophene sulfone-olefin structural unit in the present invention, the thiophene sulfone compounds, olefins, oxidants and additives are dissolved in the tetrahydrofuran solvent, and are subjected to a reaction under the catalytic action of $Pd(OAc)_2$ in the catalytic amount, and the alkenylated thiophene sulfone products (fluorescent material containing the thiophene sulfone-alkene structural unit) with obvious fluorescence emission characteristics of liquid and solid can be obtained; and the preparation method expands the range of substrates well, featuring good regional selectivity, high yield, mild reaction conditions and simple operation.

BRIEF DESCRIPTION OF THE DRAWINGS

FIG. 9A are ultraviolet and visible absorption spectra; FIG. 9B is fluorescence emission spectrum; FIG. 9C is the fluorescence image of 10-5 mol/L dichloromethane solution under the ultraviolet lamp ($\lambda_E$X=365 nm); and. FIG. 9D is the fluorescence image of solid under the ultraviolet lamp ($\lambda_{ex}$=365 nm).

DETAILED DESCRIPTION OF THE EMBODIMENTS

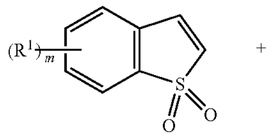

1

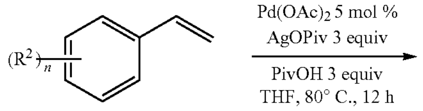

2

-continued

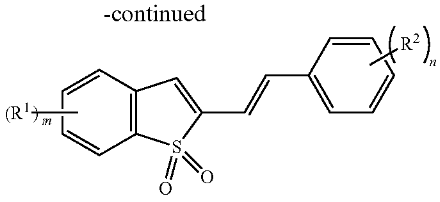

3

Figure 1:
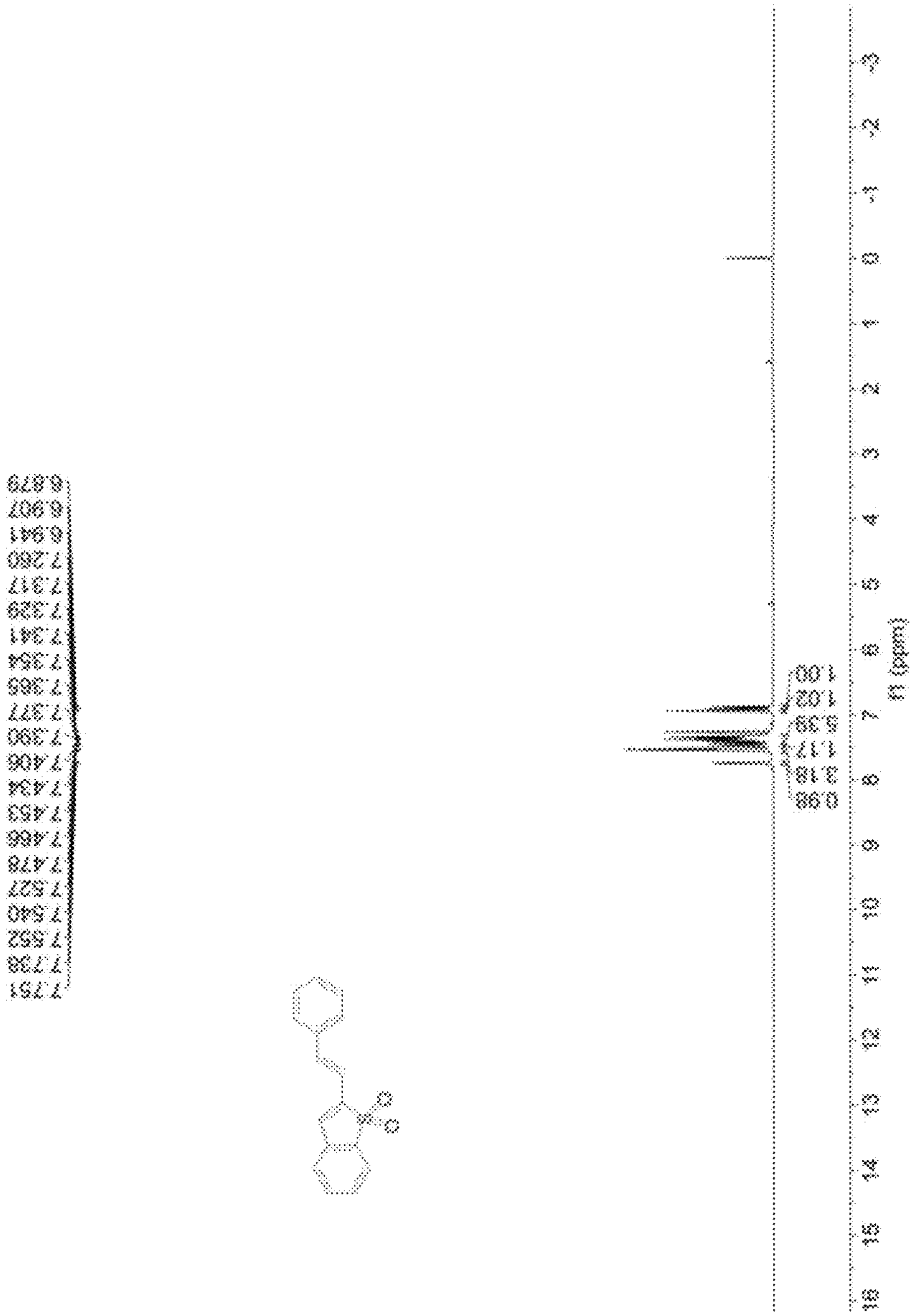
FIG. 1 shows a $^1H$ NMR spectrogram of the product prepared according to Example 1.

Benzothiophene sulfone 1 (0.2. mmol, 1.0 equiv), alkene 2 (0.3 mmol, 1.5 equiv), AgOPiv (125 mg, 0.6 mmol, 3.0 equiv), PivOH (61 mg, 0.6 mmol, 3.0 equiv) and $Pd(OAc)_2$ (2.2 mg, 5 mol %) were accurately added in a reaction tube and dissolved in 1.2 mL THF to obtain a mixture; and the mixture was reacted at 80° C. for 12 h. The reaction mixture was passed through a thin layer of celite pad and washed with ethyl acetate. Washing solvents were totally transferred to a round bottom flask, silica gel was added to the flask, and the solvents were evaporated with vacuum. EtOAc/petroleum ether was used as eluent, and silica gel column chromatography was adopted to perform the purification to obtain a corresponding product 3.

The present invention will be further described below in conjunction with specific examples.

Example 1

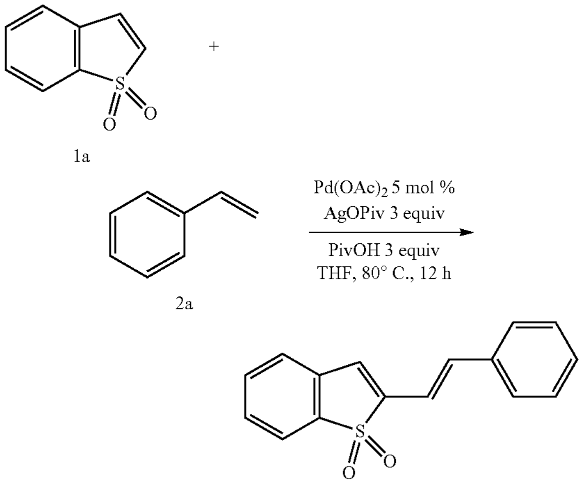

1a

2a

3a

Benzothiophene sulfone 1a (33.2 mg, 0.2 mmol, 1.0 equiv), alkene 2a (34 μL, 0.3 mmol, 1.5 equiv), AgOPiv (125 mg, 0.6 mmol, 3.0 equiv), PivOH (61 mg, 0.6 mmol, 3.0 equiv) and $Pd(OAc)_2$ (2.2 mg, 5 mol %) were accurately added in a reaction tube and dissolved in 1.2 mL THF to obtain a mixture; and the mixture was reacted at 80° C. for 12 h. The reaction mixture was passed through a thin layer of celite pad and washed with ethyl acetate. Washing solvents were totally transferred to a round bottom flask, silica gel was added to the flask, and the solvents were evaporated with vacuum. EtOAc/petroleum ether (v/v, 1:5) was used as eluent, and silica gel column chromatography was adopted to perform the purification to obtain a corresponding product 3a with a yield of 92%.

Nuclear magnetic resonance (NMR) data of the product 3a are: $^{1}H$ NMR (600 MHz, $CDCl_3$): δ=7.74 (d, J=7.8 Hz, 1H), 7.55-7.53 (m, 3H), 7.47 (t, J=7.2 Hz, 1 H), 7.41-7.32 (m, 5 H), 6.94 (s, 1 H), 6.89 (t, J=16.8 Hz, 1H) ppm.

$^{13}C$ NMR (101 MHz, $CDCl_3$): δ=141.8, 137.5, 136.3, 135.9, 133.9, 132.0, 129.8, 129.4, 129.0, 127.4, 125.1, 124.9, 121.5, 114.9 ppm.

Figure 2:
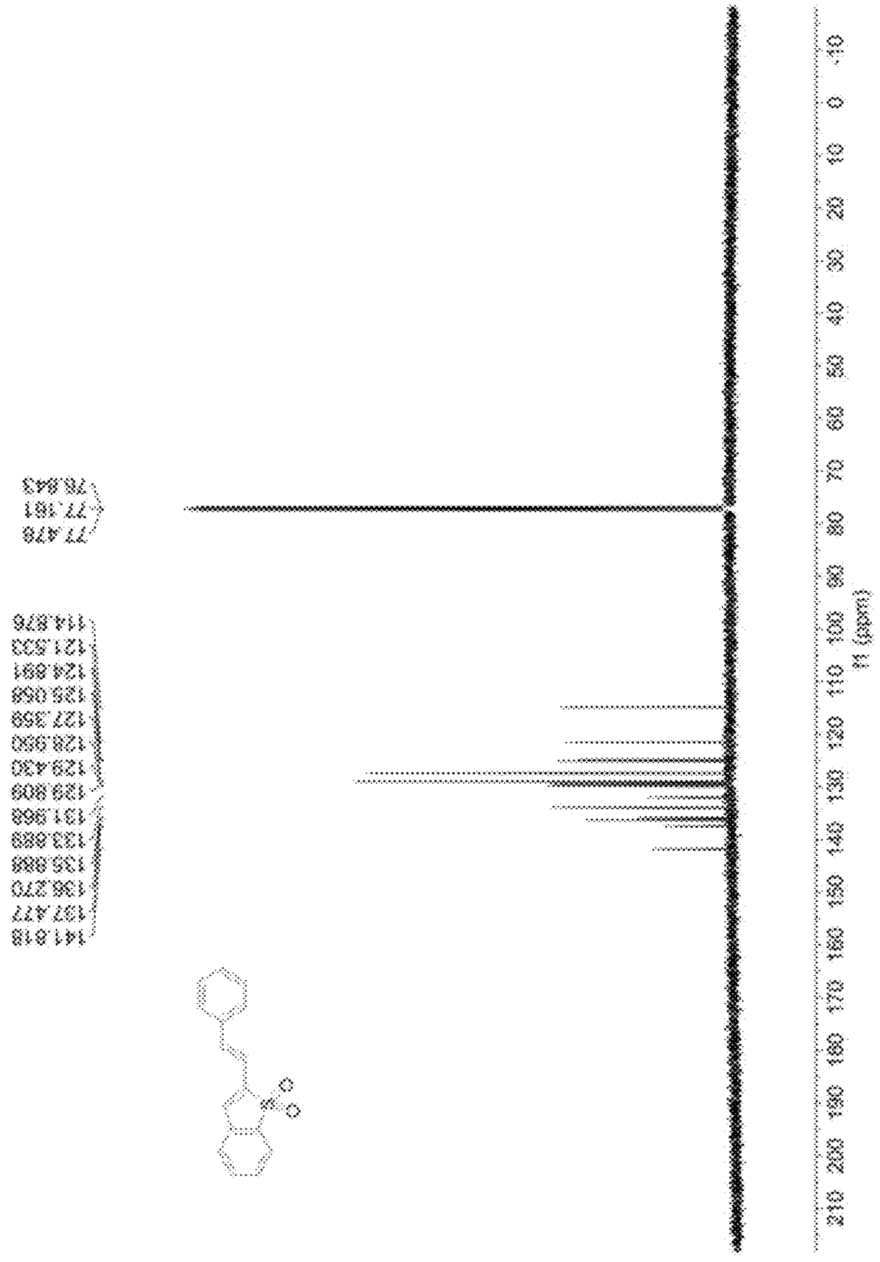
FIG. 2 shows a $^{13}C$ NMR spectrogram of the product prepared according to Example 1.

FIG. 1 shows a $^{1}H$ NMR spectrogram of the product 3a prepared according to Example 1; and FIG. 2 shows a $^{13}C$ NMR spectrogram of the product 3a prepared according to Example 1.

Example 2

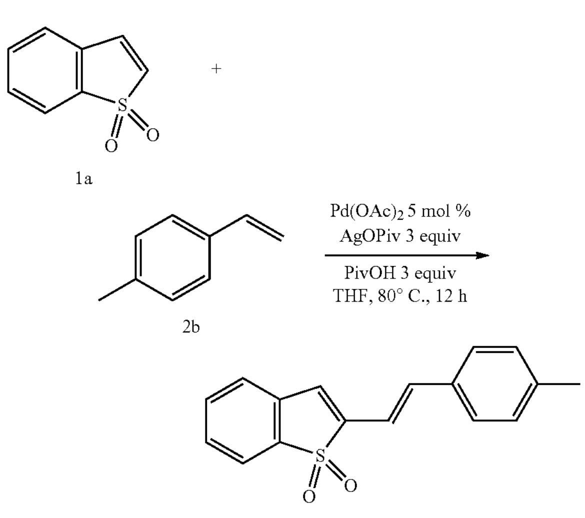

1a

2b

3b

Benzothiophene sulfone 1a (33.2 mg, 0.2 mmol, 1.0 equiv), alkene 2a (40 μL, 0.3 mmol, 1.5 equiv), AgOPiv (125 mg, 0.6 mmol, 3.0 equiv), PivOH (61 mg, 0.6 mmol, 3.0 equiv) and $Pd(OAc)_2$ (2.2 mg, 5 mol %) were accurately added in a reaction tube and dissolved in 1.2 mL THF to obtain a mixture; and the mixture was reacted at 80° C. for 12 h. The reaction mixture was passed through a thin layer of celite pad and washed with ethyl acetate. Washing solvents were totally transferred to a round bottom flask, silica gel was added to the flask, and the solvents were evaporated with vacuum. EtOAc/petroleum ether (v/v, 1:5) was used as eluent, and silica gel column chromatography was adopted to perform the purification to obtain a corresponding product 3b with a yield of 78%, Nuclear magnetic resonance (NMR) data of the product 3b are: $^{1}H$ NMR (400 MHz, $CDCl_3$): δ=7.74 (d, J=7.6 Hz,1H), 7.54 (td, J=7.6, 1.2 Hz,1H), 7.48-7.33 (m, 5H), 7.18 (d, J=8.0 Hz, 2H), 6.90 (s, 1H), 6.85 (d, J=16.4 Hz, 1H), 2.37(s, 3H) ppm.

$^{13}C$ NMR (101 MHz, $CDCl_3$): δ=142.1, 139.7, 137.5, 136.4, 133.9, 133.2, 132.1, 129.7, 129.7, 127.4, 124.9, 124.2, 121.6, 113.9, 21.6 ppm.

Figure 3:
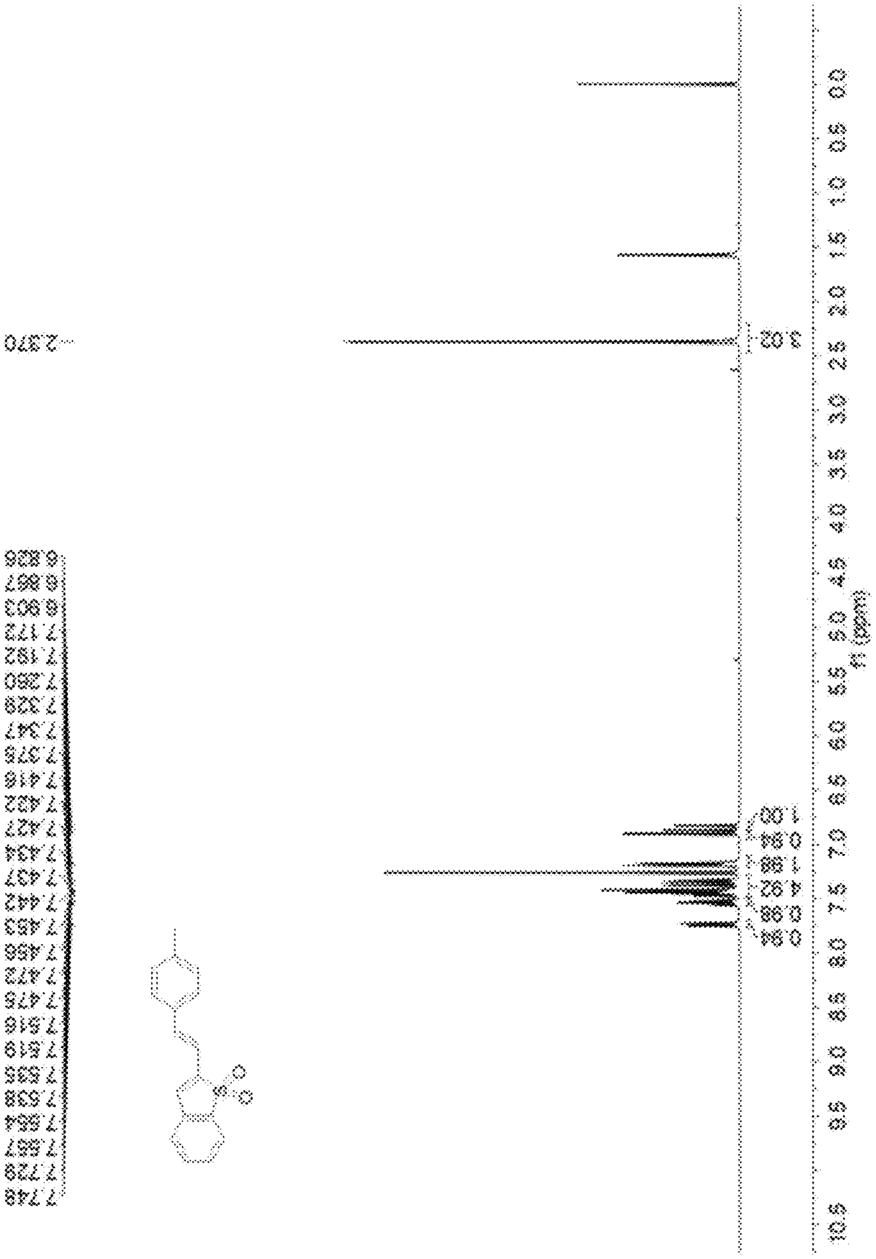
FIG. 3 shows a $^1H$ NMR spectrogram of the product prepared according to Example 2.
Figure 4:
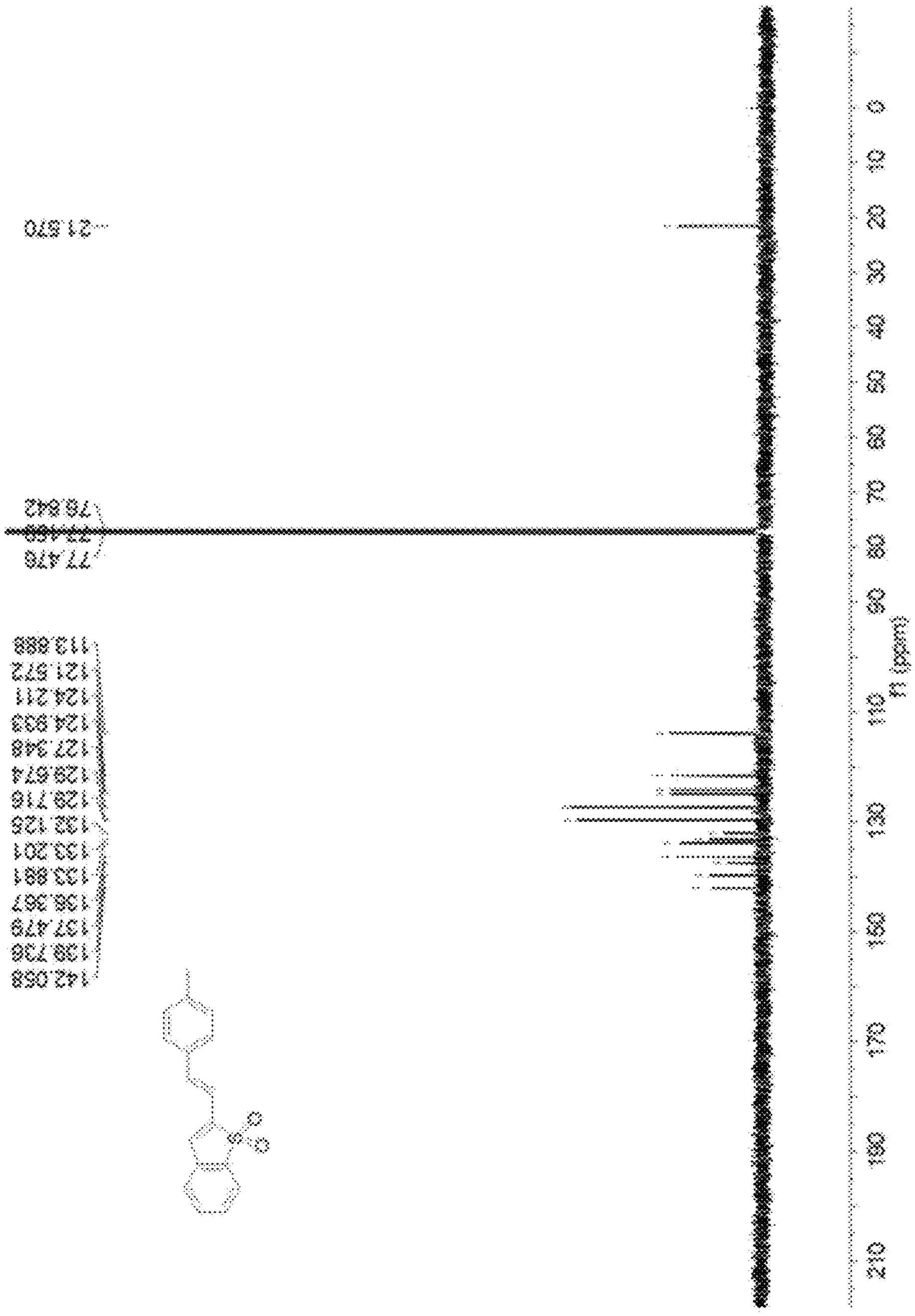
FIG. 4 shows a $^{13}C$ NMR spectrogram of the product 3a prepared according to Example 2.

FIG. 3 shows a $^{1}H$ NMR spectrogram of the product 3b prepared according to Example 2; and FIG. 4 shows a $^{13}C$ NMR spectrogram of the product 3b prepared according to Example 2.

Example 3

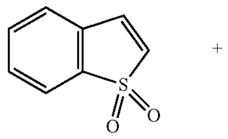

1a

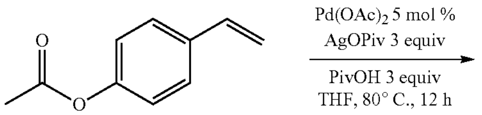

2c

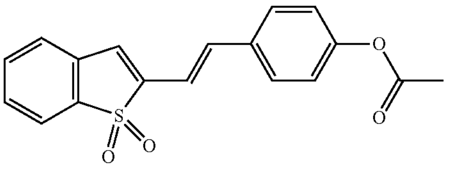

3c

Benzothiophene sulfone 1a (33.2 mg, 0.2 mmol, 1.0 equiv), alkene 2e (46 μL, 0.3 mmol, 1.5 equiv), AgOPiv (125 mg, 0.6 mmol, 3.0 equiv), PivOH (61 mg, 0.6 mmol,3.0 equiv) and $Pd(OAc)_2$ (2.2 mg, 5 mol %) were accurately added in a reaction tube and dissolved in 1.2 mL, THF to obtain a mixture; and the mixture was reacted at 80° C. for 12 h, The reaction mixture was passed through a thin layer of celite pad and washed with ethyl acetate. Washing solvents were totally transferred to a round bottom flask, silica gel was added to the flask, and the solvents were evaporated with vacuum. EtOAc/petroleum ether (v/v, 1:3) was used as eluent, and silica gel column chromatography was adopted to perform the purification to obtain a corresponding product 3c with a yield of 63%.

Nuclear magnetic resonance (NMR) data of the product 3c are: $^1$H NMR (400 MHz, $CDCl_3$): δ=7.74 (d, J=7.6 Hz, 1H), 7.56-7.52 (m, 3H), 7.46 (td, J=7.6. 1.2 Hz, 1H), 7.39(d, J=16.4 Hz, 1H), 7.34 (d, J=7.6 Hz, 1H), 7.13-7.10 (m,2H), 6.94 (d, J=0.8 Hz, 1H), 6.83 (dd, J=16.4, 0.8 Hz, 1H), 2.31 (s, 3H) ppm.

$^{13}$C NMR (101 MHz, $CDCl_3$): δ=169.4, 151.5, 141.7, 137.5, 135.1, 133.9, 133.7, 131.9, 129.9, 128.4, 125.1, 122.2, 121.6, 115.1, 21.3 ppm.

Figure 5:
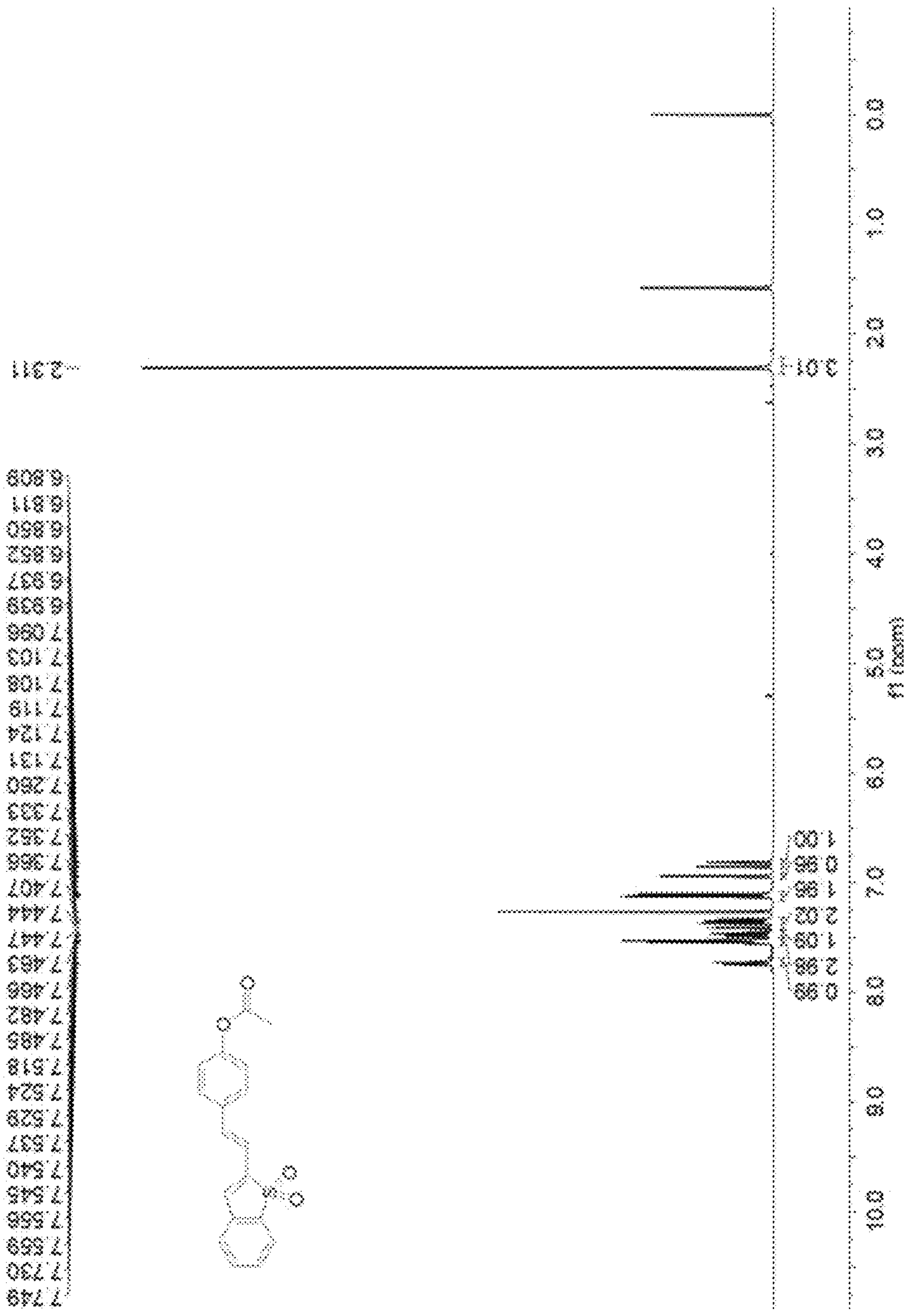
FIG. 5 shows a $^1H$ NMR spectrogram of the product prepared according to Example 3.
Figure 6:
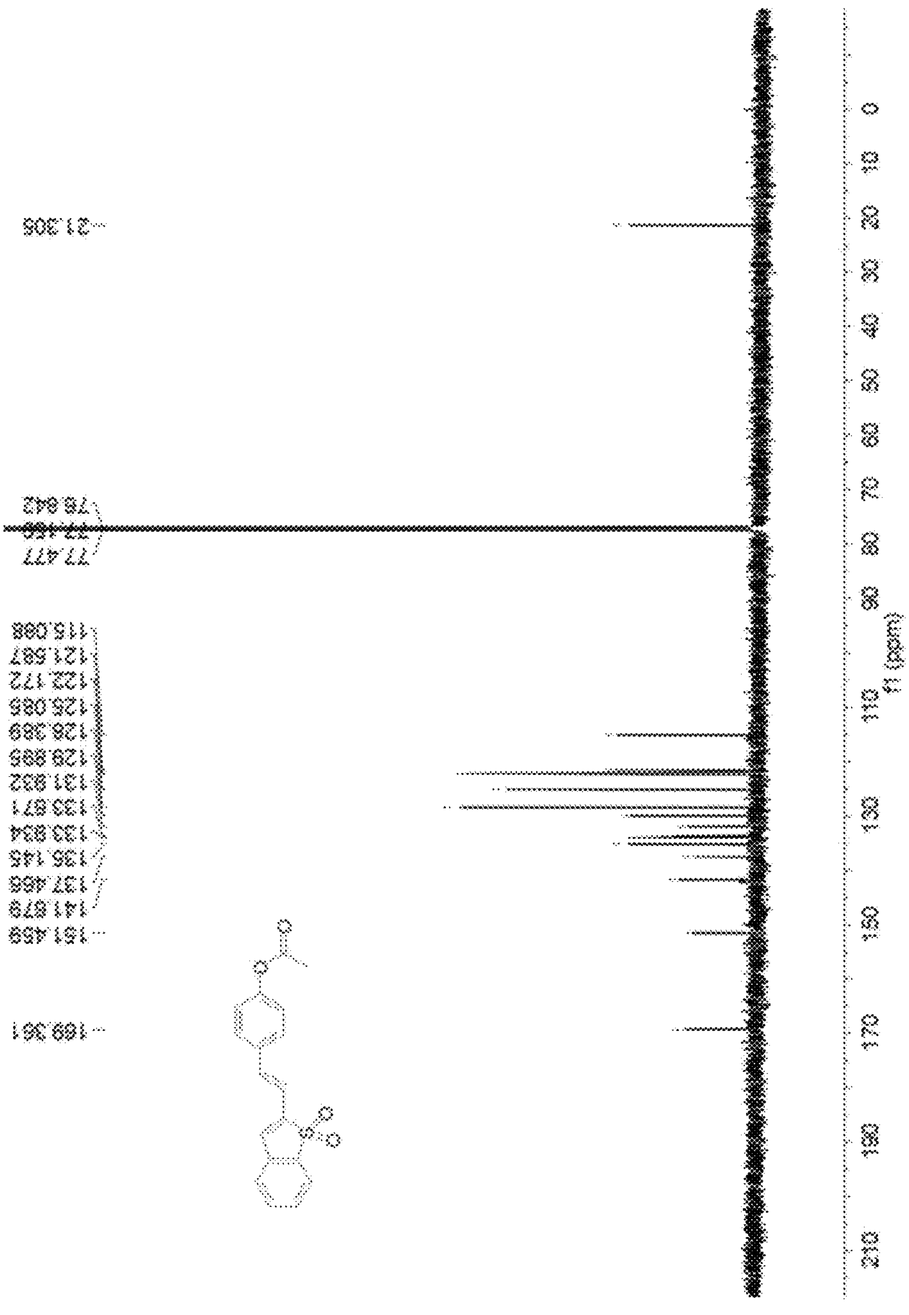
FIG. 6 shows a $^{13}C$ NMR spectrogram of the product prepared according to Example 3.

FIG. 5 shows a $^1$H NMR spectrogram of the product 3c prepared according to Example 3; and FIG. 6 shows a $^{13}$C, NMR spectrogram of the product 3e prepared according to Example 3.

Example 4

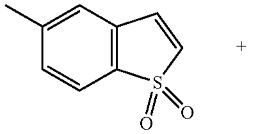

1b

-continued

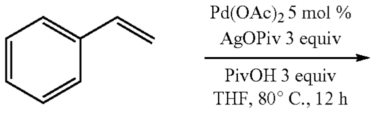

2a

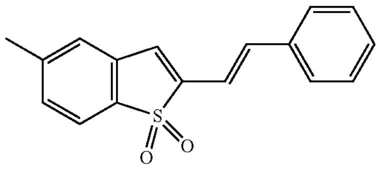

3d

Benzothiophene sulfone 1a (36 mg, 0.2 mmol, 1.0 equiv), alkene 2a (34 μL, 0.3 mmol, 1.5 equiv), AgOPiv(125 mg, 0.6 mmol, 3.0 equiv), PivOH (61 mg, 0.6 mmol,3.0 equiv) and $Pd(OAc)_2$(2.2 mg, 5 mol %) were accurately added in a reaction tube and dissolved in 1.2 mL THF to obtain a mixture; and the mixture was reacted at 80° C. for 12 h. The reaction mixture was passed through a thin layer of celite pad and washed with ethyl acetate. Washing solvents were totally transferred to a round bottom flask, silica gel was added to the flask, and the solvents were evaporated with vacuum. EtOAc/petroleum ether (v/v, 1:5) was used as eluent, and silica gel column chromatography was adopted to perform the purification to obtain a corresponding product 3d with a yield of 73%.

Reference for the synthesis of benzothiophene sulfone 1b used in this example: Ji, P.; Zhang, Y.; Dong, Y.; Huang, H.; Wei, Y. Wang, W. Synthesis of Enantioenrichedα-Deuteratedα-Amino Acids Enabled by an Organophotocatalytic Radical Approach. *Org Lett.* 2020, 22, 1557-1562.

Nuclear magnetic resonance (NMR) data of the product 3d are: $^1$H NMR (400 MHz, $CDCl_3$): δ=7.62 (d, J=7.6 Hz, 1H), 7,53-7,50 (m, 2H), 7.43-7.30 (m, 4H), 7.25 (d, J=8.0 Hz, 1H), 7.14 (s, 1H), 6.89-6.85 (m, 2H), 2.41 (s, 3H)ppm.

$^{13}$C NMR (101 MHz, $CDCl_3$): 144.9, 142.1, 136.1, 136.0, 134.8, 132.3, 130.3, 129.4, 128.9, 127.3, 125.8, 125.0, 121.4, 115.0, 21.9 ppm.

Figure 7:
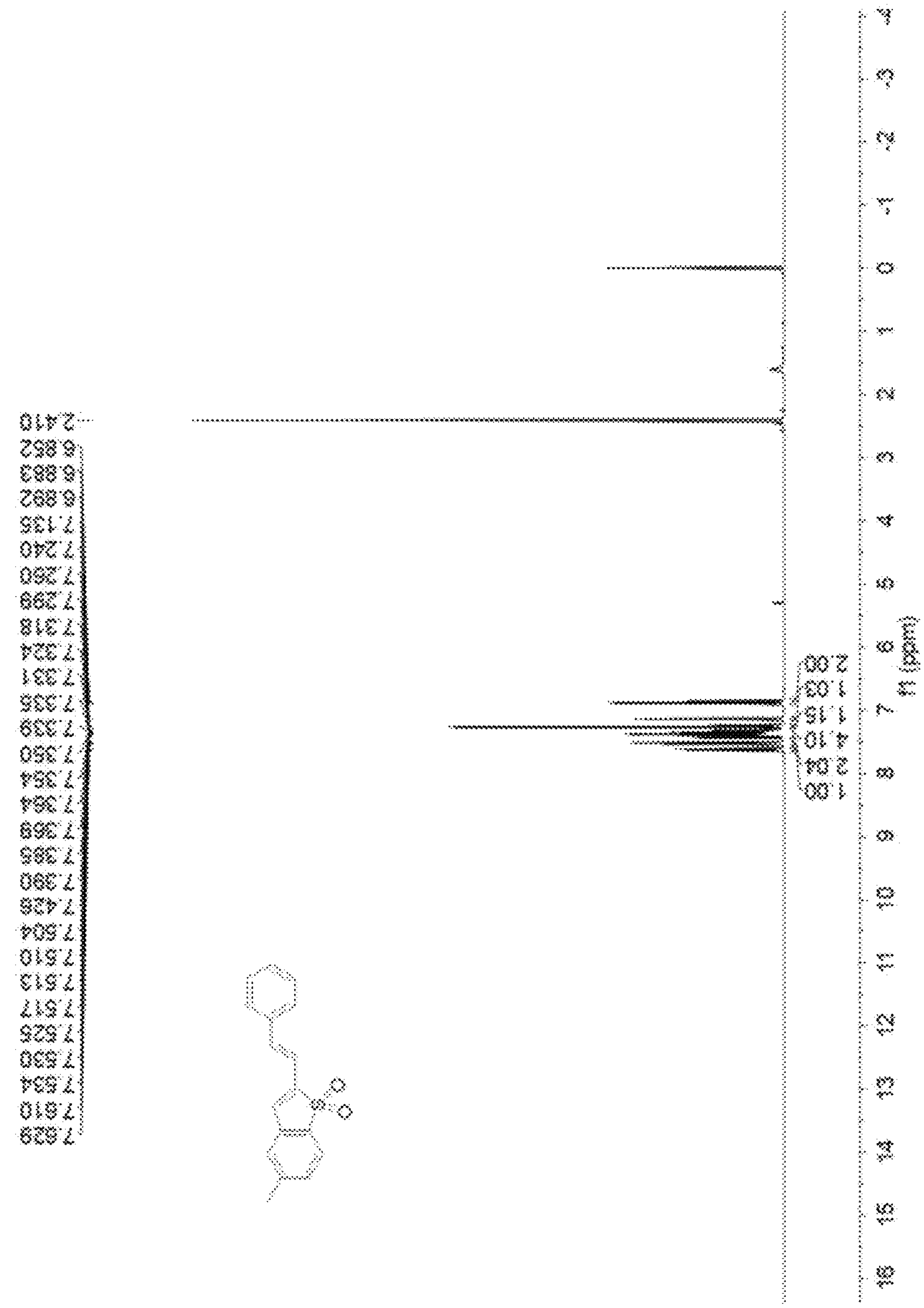
FIG. 7 shows a $^1H$ NMR spectrogram of the product prepared according to Example 4.
Figure 8:
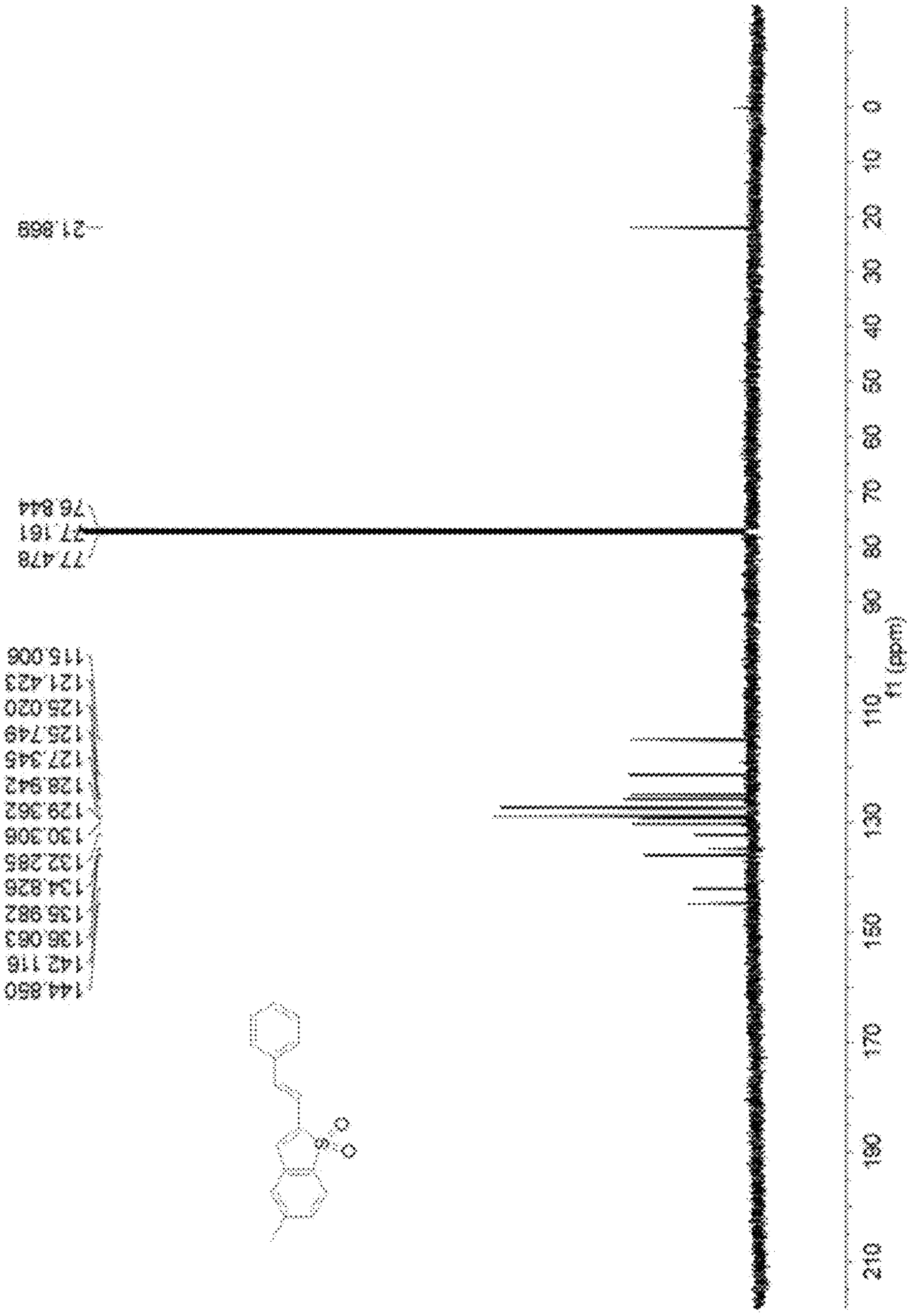
FIG. 8 shows a $^{13}C$ NMR spectrogram of the product prepared according to Example 4.

FIG. 7 shows a $^1$H NMR spectrogram of the product 3d prepared according to Example 4; and FIG. 8 shows a $^{13}$C NMR spectrogram of the product 3d prepared according to Example 4.

Example 5

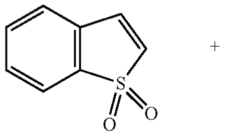

1a

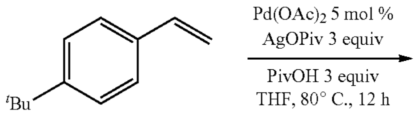

2d

-continued

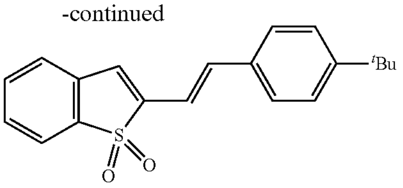

3e

Benzothiophene sulfone 1a (33.2 mg, 0.2 mmol, 1.0 equiv), alkene 2e (55 μL, 0.3 mmol, 1.5 equiv), AgOPiv (125 mg, 0.6 mmol, 3.0 equiv), PivOH (61 mg, 0.6 mmol,3.0 equiv) and $Pd(OAc)_2$ (2.2 mg, 5 mol %) were accurately added in a reaction tube and dissolved in 1.2 mL THF to obtain a mixture; and the mixture was reacted at 80° C. for 12 h. The reaction mixture was passed through a thin layer of celite pad and washed with ethyl acetate. Solvents were totally transferred to a round bottom flask, silica gel was added to the flask, and the solvents were evaporated with vacuum. EtOAc/petroleum ether (v/v, 1:6) was used as eluent, and silica gel column chromatography was adopted to perform the purification to obtain a corresponding product 3e with a yield of 94%.

Nuclear magnetic resonance (NMR) data of the product 3e are: $^{1}H$ NMR (400 MHz, DMSO-$d_6$): δ=7.89 (d, J=7.6 Hz, 1H), 7.70 (t, J=7.6 Hz, 1H), 7.64 (d, J=7.6 Hz, 1H), 7.60-7.56 (m, 3H), 7.46-7.44 (m, 3H), 7.20 (s, 2H), 1.30 (s, 9H) ppm.

$^{13}C$ NMR (101 MHz, DMSO-$d_6$) δ=152.2, 140.8, 136.7, 134.4, 134.1, 132.9, 131.4, 130.2, 127.0, 125.9, 125.8, 125.8, 121.3, 115.1, 34.6, 31.0 ppm.

Example 6

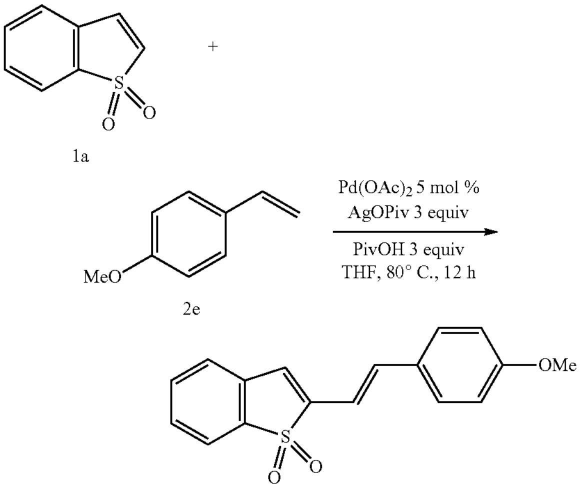

3f

Berizothiophene sulfone 1a (33.2 mg, 0.2 mmol, 1.0 equiv), alkene 2e (40 μL, 0.3 mmol, 1.5 equiv), AgOPiv (125 mg, 0.6 mmol, 3.0 equiv), (61 mg, 0.6 mmol, 3.0 equiv) and $Pd(OAc)_2$ (2.2 mg, 5 mol %) were accurately added in a reaction tube and dissolved in 1.2 mL THF to obtain a mixture; and the mixture was reacted at 80° C. for 12 h, The reaction mixture was passed through a thin layer of celite pad and washed with ethyl acetate. Washing solvents were totally transferred to a round bottom flask, silica gel was added to the flask, and the solvents were evaporated with vacuum. EtOAc/petroleum ether (v/v, 1:4) was used as eluent; and silica gel column chromatography was adopted to perform the purification to obtain a corresponding product 3f with a yield of 90%.

Nuclear magnetic resonance (NMR) data of the product 3f are: $^{1}H$ NMR NMR (400 MHz, DMSO-$d_6$): δ=7.88 (d, J=7.2 Hz, 1H), 7.69 (t, J=7.6 Hz, 1H), 7.63-7.54 (m, 4H), 7.38 (s,1H), 7.18 (d, J=16.8 Hz, 1H), 7.10 (d, J=16.8 Hz, 1H), 6.99 (d, J=8.4 Hz, 2H), 3.80 (s, 3H) ppm.

$^{13}C$ NMR (101 MHz, DMSO-$d_6$): δ=160.3, 141.0, 136.6, 134.3, 134.1, 131.6, 129.9, 128.7, 128.2, 125.6, 124.8, 121.2, 114.5, 113.5, 55.3 ppm.

Example 7

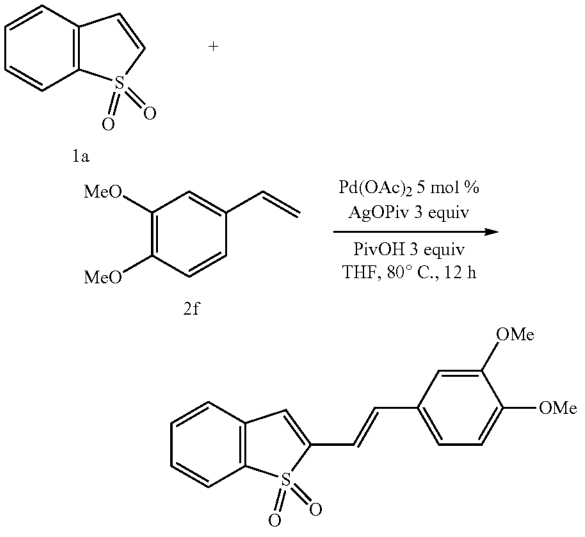

3g

Benzothiophene sulfone 1a (33.2 mg, 0.2 mmol, 1.0 equiv), alkene 2f (44 μL, 0.3 mmol, 1.5 equiv), AgOPiv (125 mg, 0.6 mmol, 3.0 equiv), PivOH (61 mg, 0.6 mmol, 3.0 equiv) and. $Pd(OAc)_2$ (2.2 mg, 5 mol %) were accurately added in a reaction tube and dissolved in 1.2 mL THE to obtain a mixture; and the mixture was reacted at 80° C. for 12 h. The reaction mixture was passed through a thin layer of celite pad and washed with ethyl acetate. Washing solvents were totally transferred to a round bottom flask, silica gel was added to the flask, and the solvents were evaporated with vacuum. EtOAc/petroleum ether (v/v, 1:3) was used as eluent, and silica gel column chromatography was adopted to perform the purification to obtain a corresponding product 3 g with a yield of 77%.

Nuclear magnetic resonance (NMR) data of the product 3 g are: $^{1}H$ NMR (400 MHz, $CDCl_3$): δ=7.73 (d, J=7.2 Hz, 1H), 7.52 (td, J=7.6, 0.8 Hz, 1H), 7.44 (td, J=7.6, 1.2 Hz, 1H), 7.37-7.30 (m, 2H), 7.12 (dd, J=8.4, 2.0 Hz, 1H), 7.03 (d, J =2.0 Hz, 1H), 6.87-6.85 (m, 2H), 6.76 (d, J=16.4 Hz, 1H), 3.93 (s, 3H), 3.91 (s, 3H) ppm.

$^{13}C$ NMR(101 MHz, $CDCl_3$): δ=150.4, 149.3, 142.0, 137.3, 136.1, 133.9, 132.2, 129.5, 129.0, 124.9, 123.6. 121.5, 121.1, 112.9, 111.3, 109.6, 56.1, 56.0 ppm,

Example 8

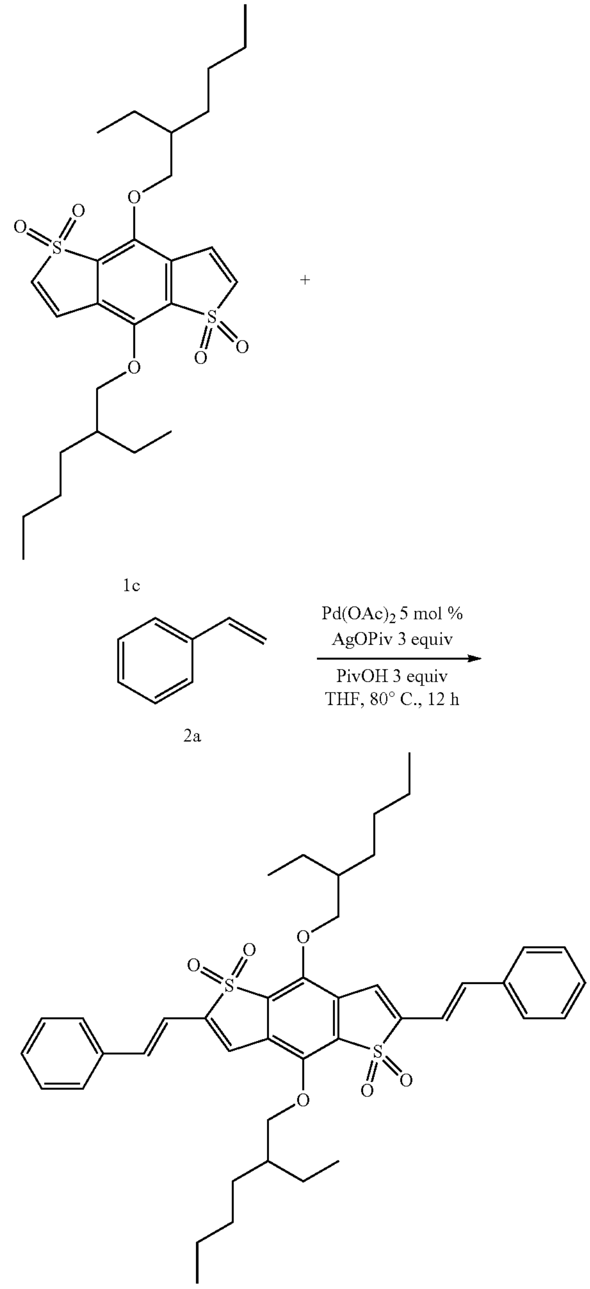

1c

2a

4

Benzothiophene sulfone 1a (33.2. mg, 0.2. mmol; 1.0 equiv), alkene 2a (69 μL, 0.6 mmol, 1.5 equiv), AgOPiv (125 mg, 0.6 mmol, 3.0 equiv), (61 mg, 0,6 mmol, 3.0 equiv) and $Pd(OAc)_2$ (2.2 mg, 5 mol %) were accurately added in a reaction tube and dissolved in 1.2 mL THF to obtain a mixture; and the mixture was reacted at 80° C. for 12 h, The reaction mixture was passed through a thin layer of celite pad and washed with ethyl acetate. Washing solvents were totally transferred to a round bottom flask, silica gel was added to the flask, and the solvents were evaporated with vacuum. EtOAc/petroleum ether (v/v, 1:3) was used as eluent, and silica gel column chromatography was adopted to perform the purification to obtain a corresponding product 4 with a yield of 78%.

Reference for the synthesis of benzothiophene sulfone 1c used in this example: Pappenfus, T. M.; Seidenkranz, D. T.; Lovander, M. D.; Beck, T. I.; Karels, B. Ogawa, K.; Janzen, D. E. Synthesis and Electronic Properties of Ofiduzed Benzo dithiophenes. *J. Org. Chem.* 2014, 79, 9408-9412.

Nuclear magnetic resonance (NMR) data of the product 4 are: $^1H$ NMR (600 MHz, $CDCl_3$): δ=7.55 (d, J=7.2 Hz, 4H), 7.44-7.36 (m, 8H), 7.07 (s, 2H), 6.91 (d, J=16.2 Hz, 2H), 4.40 (dd, J=5.4 Hz, 1.2 Hz, 4H), 1.88-1.84 (m, 2H), 1.65-1.59 (m, 2H), 1.58-1.47 (m, 6H), 1.42-1.36 (m, 8H), 1.02 (t, I=7.2 Hz, 6H), 0.95 (t, I=7.2 Hz, 6H) ppm. 6H), 1.42-1.36 (m, 8H), 1.02 (t, J=7.2 Hz, 6H), 0.95 (t, J=7.2 Hz, 6H) ppm.

$^{13}C$ NMR (101 MHz, $CDCl_3$): δ=145.3, 141.8, 137.1, 135.8, 131.8, 129.8, 129.1, 128.1, 127.5, 119.5, 114.9, 79.1, 40.6, 30.4, 29.2, 23.8, 23.2, 14.3, 11.3 ppm.

Photophysical Properties of some Products

Figure 9A:
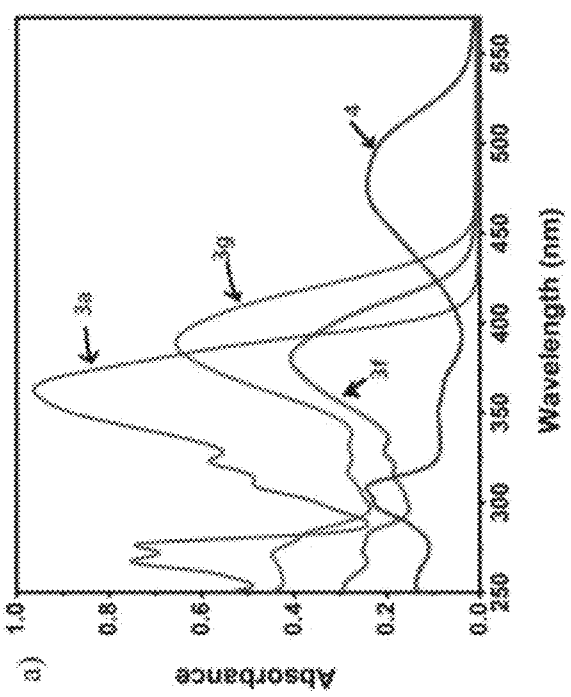
FIGS. 9A-9D show the test results of photophysical properties of the products prepared according to the examples, specifically.
Figure 9B:
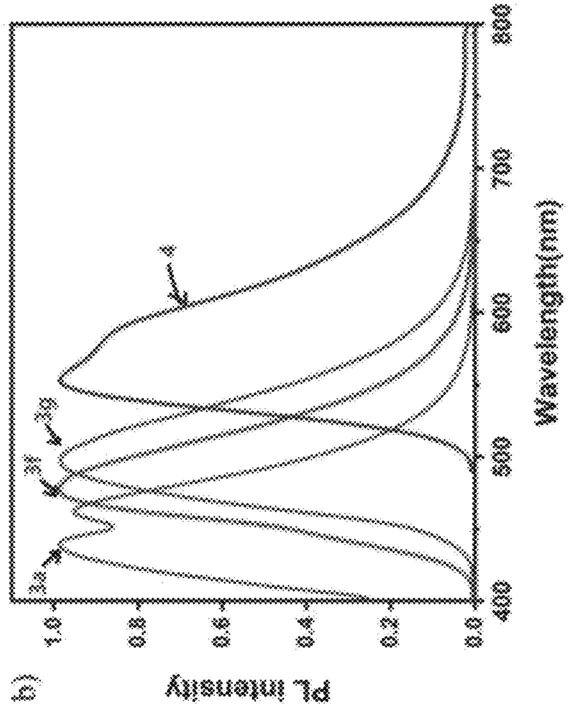
Figure 9C:
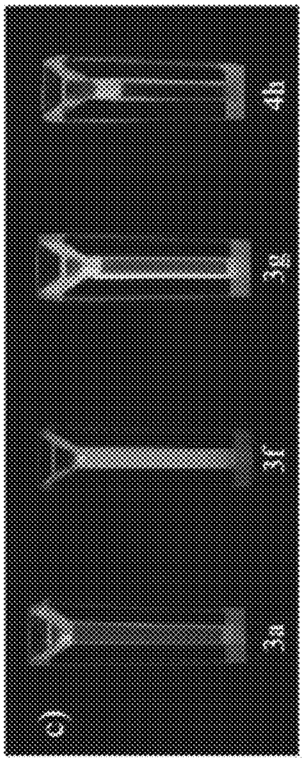
Figure 9D:
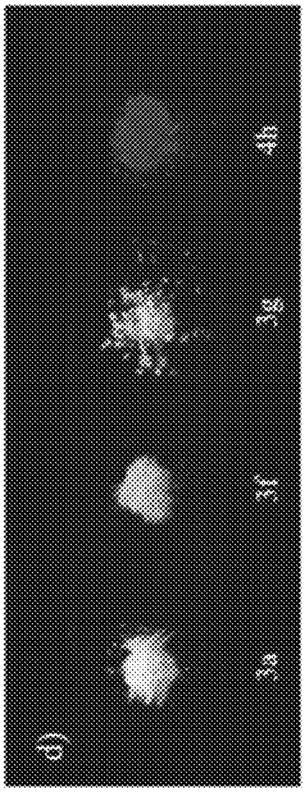

The products 3a; 3f; 3 g and 4 were dissolved in methylene chloride respectively to prepare a solution of 10-5 mol/L. The ultraviolet and visible absorption spectra were tested, and the test results were shown in FIGS. 9A-9D. It can be seen from FIG. 9A that the maximum absorption wavelengths of 3a. 3f and 3 g are 363 nm, 379 nm and 389 nm, respectively; the dienylated product 4 has a larger π-conjugated system, and its maximum absorption wavelength is redshifted to 474 nm. It can be seen from FIG. 9B that the fluorescence emitted by the products 3a, 3f, 3 g and 4 is in the region of blue light to orange light. In addition, 3a, 3f, 3 g and 4 exhibit obvious fluorescence emission characteristics of liquid and solid, as shown in FIGS. 9C-9D.

What is claimed is:

1. A fluorescent material containing a thiophene sulfone-olefin structural unit, wherein a structural formula of the fluorescent material containing the thiophene sulfone-olefin structural unit is as follows:

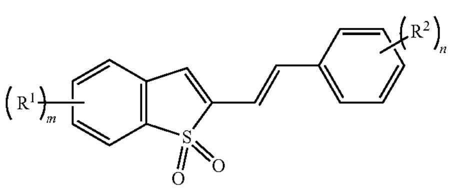

in the structural formula, $R^1$ is one of H, alkyl, and alkoxy group; m=1-4; when m≠1, a plurality of $R^1$s is separately selected as one of the H, the alkyl, and the alkoxy group; and $R^2$ is one of H, alkyl group, alkoxy group, and aryl group; n=1-5; when n≠1, a plurality of $R^2$s is separately selected as one of the H, the alkyl group, the alkoxy group, and the aryl group.

2. A preparation method of the fluorescent material containing the thiophene sulfone-olefin structural unit according to claim 1, comprising:

in a presence of a palladium catalyst, subjecting a thiophene sulfone compound, olefin, an oxidant, and an additive to an oxyalkylene reaction in a solvent to obtain a reaction mixture, and after the oxyalkylene reaction is completed, performing a post-treatment on the reaction mixture to obtain the fluorescent material containing the thiophene sulfone-olefin structural unit;

wherein a structural formula of the thiophene sulfone compound is shown in Formula (I):

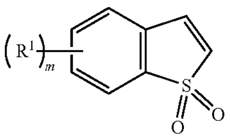

(I)

a structural formula of the olefin is shown in Formula (II):

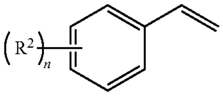

(II)

in the Formulas (I)-(II), $R^1$ is one of H, alkyl, and alkoxy group; m=1-4; when m≠1, a plurality of $R^1$s is separately selected as one of the H, the alkyl, and the alkoxy group; and $R^2$ is one of H, alkyl group, alkoxy group, and aryl group; n=1-5; when n≠1, a plurality of $R^2$s is separately selected as one of the H, the alkyl group, the alkoxy group, and the aryl group.

3. The preparation method of the fluorescent material containing the thiophene sulfone-olefin structural unit according to claim 2, wherein a molar ratio of the thiophene sulfone compound to the olefin is 1:(1-3).

4. The preparation method of the fluorescent material containing the thiophene sulfone-olefin structural unit according to claim 2, wherein the oxidant is one or more of a silver carbonate, a silver acetate, a silver oxide, and/or a silver pivalate; and a molar ratio of the thiophene sulfone compound to the oxidant is 1:(1-5).

5. The preparation method of the fluorescent material containing the thiophene sulfone-olefin structural unit according to claim 2, wherein the additive is one or more of PivOH, AcOH, and/or $CF_3COOH$; and a molar ratio of the thiophene sulfone compound to the additive is 1:(3-5).

6. The preparation method of the fluorescent material containing the thiophene sulfone-olefin structural unit according to claim 2, wherein the solvent is at least one of toluene, 1, 2-dichloroethane, 1, 4-dioxane, dimethyl sulfoxide, and/or tetrahydrofuran (THF).

7. The preparation method of the fluorescent material containing the thiophene sulfone-olefin structural unit according to claim 2, wherein the palladium catalyst is $Pd(OAc)_2$ (CAS:3375-31-3); and an amount of the palladium catalyst is 1-5 mol % of an amount of the thiophene sulfone compound.

8. The preparation method of the fluorescent material containing the thiophene sulfone-olefin structural unit according to claim 2, wherein a reaction temperature of the oxyalkylene reaction is 80-120° C.

9. The preparation method of the fluorescent material containing the thiophene sulfone-olefin structural unit according to claim 2, wherein after the oxyalkylene reaction is completed, performing the post-treatment comprises:

allowing the reaction mixture to pass through a layer of diatomaceous earth and washing with ethyl acetate to obtain a washing solution, using ethyl acetate/petroleum ether as an eluent and purifying the washing solution by a silica gel column chromatography to obtain the fluorescent material containing the thiophene sulfone-olefin structural unit.

* * * * *